(12) United States Patent
Farazi

(10) Patent No.: US 7,756,571 B1
(45) Date of Patent: Jul. 13, 2010

(54) METHODS AND SYSTEMS FOR DETECTING THE PRESENCE OF T-WAVE ALTERNANS

(75) Inventor: Taraneh Ghaffari Farazi, San Jose, CA (US)

(73) Assignee: Pacesetter, Inc., Sunnyvale, CA (US)

(*) Notice: Subject to any disclaimer, the term of this patent is extended or adjusted under 35 U.S.C. 154(b) by 944 days.

(21) Appl. No.: 11/229,411

(22) Filed: Sep. 16, 2005

(51) Int. Cl.
  *A61B 5/04* (2006.01)
  *A61B 5/0452* (2006.01)
(52) U.S. Cl. .................... 600/517; 600/509
(58) Field of Classification Search ............ 600/517
  See application file for complete search history.

(56) References Cited

U.S. PATENT DOCUMENTS

| | | | |
|---|---|---|---|
| 4,556,062 A | 12/1985 | Grassi et al. | |
| 4,665,919 A | 5/1987 | Mensink et al. | |
| 4,766,902 A | 8/1988 | Schroeppel | |
| 4,802,491 A | 2/1989 | Cohen et al. | |
| 4,974,598 A | 12/1990 | John | |
| 5,097,832 A | 3/1992 | Buchanan .................. 128/419 | |
| 5,148,812 A | 9/1992 | Verrier et al. | |
| 5,197,480 A | 3/1993 | Gebhardt | |
| 5,265,617 A | 11/1993 | Verrier et al. | |
| 5,300,092 A | 4/1994 | Schaldach | |
| 5,330,507 A | 7/1994 | Schwartz | |
| 5,391,187 A * | 2/1995 | Freeman ..................... 607/5 | |
| 5,437,285 A | 8/1995 | Verrier et al. | |
| 5,466,254 A | 11/1995 | Helland | |
| 5,476,483 A | 12/1995 | Bornzin et al. | |
| 5,547,285 A | 8/1996 | Hutzel et al. | |
| 5,549,650 A | 8/1996 | Bornzin et al. | |
| 5,560,370 A * | 10/1996 | Verrier et al. ............... 600/518 | |
| 5,570,696 A | 11/1996 | Arnold et al. | |
| 5,658,317 A | 8/1997 | Haefner et al. | |

(Continued)

FOREIGN PATENT DOCUMENTS

WO    WO 0234123 A2    2/2002

(Continued)

OTHER PUBLICATIONS

Bronzino, The Biomedical Enegineering Handbook, CRC Press, 2nd edition, vol. 1, p. 77-1.*

(Continued)

*Primary Examiner*—Carl H Layno
*Assistant Examiner*—Natasha N Patel
(74) *Attorney, Agent, or Firm*—Steven M. Mitchell

(57) ABSTRACT

Embodiments of the present invention relate to implantable systems, and method for use therein, that can detect T-wave alternans. In accordance with specific embodiments of the present invention, intrinsic premature contractions of the ventricles are detected, and at least one metric of T-waves is measured in a specified number of beats that follow each detected intrinsic premature contraction of the ventricles. A determination of whether T-wave alternans are present is made based on the measured T-wave metrics. In alternative embodiments, rather than waiting for intrinsic premature contractions of the ventricles, premature contractions of the ventricles are caused on demand by inducing premature atrial contractions. In still other embodiments, a patient's vagus nerve is stimulated to simulate premature contractions of the ventricles. This abstract is not intended to be a complete description of, or limit the scope of, the invention.

15 Claims, 7 Drawing Sheets

U.S. PATENT DOCUMENTS

| | | | | |
|---|---|---|---|---|
| 5,772,691 | A | 6/1998 | Routh et al. | 607/9 |
| 5,842,997 | A | 12/1998 | Verrier et al. | |
| 5,861,012 | A | 1/1999 | Stroebel | |
| 5,921,940 | A | 7/1999 | Verrier et al. | |
| 5,983,138 | A | 11/1999 | Kramer | 607/9 |
| 6,016,443 | A | 1/2000 | Ekwall | |
| 6,058,328 | A | 5/2000 | Levine et al. | |
| 6,169,919 | B1 | 1/2001 | Nearing et al. | |
| 6,253,107 | B1 | 6/2001 | Albrecht et al. | |
| 6,493,586 | B1 | 12/2002 | Stahmann et al. | |
| 6,735,466 | B1 | 5/2004 | Haghighi-Mood | |
| 6,823,213 | B1 | 11/2004 | Norris et al. | |
| 6,865,414 | B1 | 3/2005 | Levine | |
| 6,915,156 | B2 * | 7/2005 | Christini et al. | 600/509 |
| 6,915,157 | B2 | 7/2005 | Bennett et al. | 600/513 |
| 2001/0007948 | A1 | 7/2001 | Stoop et al. | |
| 2001/0020136 | A1 * | 9/2001 | Sweeney et al. | 600/515 |
| 2002/0138106 | A1 | 9/2002 | Christini et al. | |
| 2002/0143265 | A1 | 10/2002 | Ackerman et al. | |
| 2002/0165586 | A1 | 11/2002 | Hill | |
| 2003/0060724 | A1 | 3/2003 | Thiagarajan et al. | |
| 2003/0060854 | A1 | 3/2003 | Zhu | |
| 2003/0199937 | A1 | 10/2003 | Carlson et al. | |
| 2004/0158292 | A1 | 8/2004 | Sheldon | |
| 2005/0004608 | A1 | 1/2005 | Bullinga | 607/9 |
| 2006/0116596 | A1 * | 6/2006 | Zhou et al. | 600/516 |

FOREIGN PATENT DOCUMENTS

| | | | |
|---|---|---|---|
| WO | WO 0234123 | A3 | 2/2002 |
| WO | WO 2004/062486 | A2 | 7/2004 |
| WO | WO 2004/062486 | A3 | 7/2004 |

OTHER PUBLICATIONS

Bullinga et al., "Resonant Pacing Improves T-wave Alternans Testing in Patients with Dilated Cardiomyopathy" (Heart Rhythm v1:S129, 2004).

Narayan et al. "Demonstration of the Proarrhythmic Preconditioning of Single Premature Extrastimuli by Use of the Magnitude, Phase and Distribution of Repolarization Alternans" (Circulation. 1999; 100: 1887-1893).

Armoundas et al., Pathophusiological Basis and Clinical Application of T-Wave Alternans, Journal of the American College of Cardiology 2002;40;207-217.

Christini et al., "Endocardial Detection of Repolarization Alternans," IEE Transactions on Biomedical Engineering; vol. 50, No. 7 (2003), pp. 855-862.

Non-Final Office Action mailed Oct. 31, 2007: Related U.S. Appl. No. 11/229,407.

Final Office Action mailed Apr. 24, 2008: Related U.S. Appl. No. 11/229,407.

Final Office Action mailed Nov. 28, 2008: Related U.S. Appl. No. 11/229,407.

Non-Final Office Action mailed Jan. 22, 2008: Related U.S. Appl. No. 11/229,410.

Final Office Action mailed Nov. 24, 2008: Related U.S. Appl. No. 11/229,410.

Non-Final Office Action mailed Aug. 20, 2008: Related U.S. Appl. No. 11/341,086.

Non-Final Office Action mailed Jul. 27, 2005: Related U.S. Appl. No. 10/186,069.

Notice of Allowance mailed Nov. 21, 2005: Related U.S. Appl. No. 10/186,069.

Non-Final Office Action mailed Dec. 13, 2005: Related U.S. Appl. No. 10/868,240.

Final Office Action mailed Apr. 28, 2006: Related U.S. Appl. No. 10/868,240.

Non-Final Office Action mailed Aug. 2, 2006: Related U.S. Appl. No. 10/868,240.

Notice of Allowance mailed Mar. 28, 2007: Related U.S. Appl. No. 10/868,240.

Non-Final Office Action mailed Feb. 10, 2009: Related U.S. Appl. No. 11/229,410.

Final Office Action mailed Feb. 5, 2009: Related U.S. Appl. No. 11/341,086.

Non-Final Office Action mailed Oct. 27, 2009: Related U.S. Appl. No. 11/229,410.

Non-Final Office Action mailed Aug. 12, 2009: Related U.S. Appl. No. 11/341,086.

Atlas of Heart Diseases Arrhythmias: Electrophysciologic Principles, vol. IX, Current Medicine 1996, Fig. 6-16.

* cited by examiner

METHODS AND SYSTEMS FOR DETECTING THE PRESENCE OF T-WAVE ALTERNANS

CROSS REFERENCE TO RELATED APPLICATIONS

The present invention relates to the following commonly assigned applications, each of which is incorporated herein by reference: U.S. patent application Ser. No. 10/186,069, filed Jun. 28, 2002, entitled "Implantable Cardiac Device Having a System for Detecting T-Wave Alternan Patterns and Method," filed Jun. 28, 2002; U.S. patent application Ser. No. 10/868,240, entitled "Implantable Cardiac Device Providing Rapid Pacing T-wave Alternan Pattern Detection and Method," filed Jun. 14, 2004; U.S. patent application Ser. No. 11/229,407, entitled "Methods and Systems for Detecting the Presence of T-Wave Alternans," filed Sep. 16, 2005; and U.S. patent application Ser. No. 11/229,410, entitled "Methods and Systems for Detecting the Presence of T-Wave Alternans," filed Sep. 16, 2005.

FIELD OF THE INVENTION

The present invention generally relates to an implantable cardiac device that delivers electrical therapy to a patient's heart. The present invention more particularly relates to such a device capable of detecting T-wave alternan patterns.

BACKGROUND

Electrical alternans relate to the differences in electrical potential at corresponding points between alternate heartbeats. T-wave alternans or alternation is a regular or beat-to-beat variation of the ST-segment or T-wave of an electrocardiogram (ECG) which repeats itself every two beats and has been linked to underlying cardiac instability. Typically, by enumerating all consecutive heart beats of a patient, beats with an odd number are referred to as "odd beats" and beats with an even number are referred to as "even beats." A patient's odd and even heartbeats may exhibit different electrical properties of diagnostic significance which can be detected by an ECG.

The presence of these electrical alternans is significant because patients at increased risk for ventricular arrhythmia's commonly exhibit alternans in the ST-segment and the T-wave of their ECG. Clinicians may therefore use these electrical alternans as a noninvasive marker of vulnerability to ventricular tachyarrhythmias. The term T-wave alternans (TWA) is used broadly to denote electrical alternans such as these. It should be understood that the term encompasses both the alternans of the T-wave segment and the ST-segment of an ECG.

T-wave alternans (TWA) has been demonstrated in many studies as a strong predictor of mortality, independent of left ventricular ejection fraction (LVEF). More specifically, it has become well known that T-wave alternans has predictive value for arrhythmic events such as tachyarrhythmias. Additionally, T-wave alternans has been determined to be an indicator of various forms of disordered ventricular repolarization, including disorders found in patients with cardiomyopathy, mild to moderate heart failure, and congestive heart failure.

T-wave alternans (TWA) may be caused by changes in ion exchange during repolarization. If there is a change in the repolarization mechanism on one beat, the heart attempts to readjust on the following beat. This is manifested as an alternating change in the action potential. In the surface ECG this is seen primarily as an amplitude change. For an implanted medical device such as a cardiac pacemaker, the intracardiac electrogram (IEGM) also shows a change in timing. Thus, the term T-wave as used herein may refer to a portion of the ventricular QRS-T-wave complex that includes the T-wave and the QRS-T segment. The alternating feature of TWA can be detected by examination, for example, of the QT interval, T-wave width, T-wave amplitude and morphology, etc. Whatever the designated portion of the intracardiac electrogram, T-wave alternans refers to an alternating pattern of the wave that can be designated "A-B-A-B-A . . ." where A represents every other cycle and B represents every other alternate cycle. As discussed in the literature, when such an alternating pattern appears, the different rates or forms of repolarization of the ventricular cells are statistically associated with a variety abnormal cardiac conditions. Further, the alternating repolarization pattern can lead to increased instability and consequent cardiac arrhythmias. Thus, the presence of T-wave alternans is recognized as an indicator of risk for ventricular arrhythmia and even sudden cardiac death (SCD).

In the past, detection of T-wave alternan patterns has been performed using surface ECGs. Implementation of such detection has included the measurement, on a beat-to-beat basis, of the micro-volt level changes in the T-wave amplitude from the surface ECG. Then, the long record of time series of T-wave amplitude change is transformed into the frequency domain by Fourier series transformation (FFT). A prominent peak in the FFT at 0.5 Hz would verify the existence of a T-wave alternan pattern.

Unfortunately, the above detection method requires the use of medical equipment that must be operated by medical personnel in a medical facility such as a physician's office. The detection requires long term recording of surface ECGs and off-line analysis with robust computation equipment. As a result, T-wave alternan pattern monitoring has been inconvenient and cumbersome. As a result, it is difficult to provide continuous and regular T-wave alternan pattern monitoring.

Many patients who would benefit from T-wave alternan pattern monitoring have an implanted cardiac device such as an implantable defibrillator or a combined defibrillator pacemaker. It would thus be highly desirable if such an implanted device could monitor for T-wave alternan patterns. However, the prior art detection method does not lend itself for such application due to, for example, the required long term monitoring, surface ECG, and robust computational requirements for Fourier series transformation.

In order for an implanted cardiac device to provide T-wave alternan pattern monitoring, there is a need for a new and different approach. The present invention addresses that need.

BRIEF SUMMARY OF THE INVENTION

Embodiments of the present invention relate to implantable systems, and methods for use therein, that can detect T-wave alternans. In accordance with specific embodiments of the present invention, intrinsic premature contractions of the ventricles are detected, and at least one metric (e.g., T-wave amplitude) of T-waves is measured in a specified number of beats (e.g., anywhere from 2 to 10 beats) that follow each detected intrinsic premature contraction of the ventricles. A determination of whether T-wave alternans are present is made based on the measured T-wave metrics.

In accordance with certain embodiments, whenever one of the detected intrinsic premature contractions of the ventricles is not immediately preceded by at least a specified number of (e.g., 3) non-premature contractions of the ventricles, then T-wave metrics are not measured for the beats that follow that detected intrinsic premature contraction of the ventricles. Alternatively, whenever one of the detected intrinsic premature contractions of the ventricles is not immediately preceded by at least a specified number of non-premature contractions of the ventricles, then the T-wave metrics measured for the beats that follow that detected intrinsic premature contraction of the ventricles are not used when determining whether T-wave alternans are present.

In other embodiments, premature contractions of the ventricles are induced during intrinsic sinus rhythm, and at least one metric of T-waves is measured in a specified number of beats that follow each induced premature contraction of the ventricles. A determination of whether T-wave alternans are present is made based on the measured T-wave metrics.

In alternative embodiments, premature contractions of the ventricles are caused by inducing premature atrial contractions, and at least one metric (e.g., T-wave amplitude) of T-waves is measured in a specified number of beats (e.g., anywhere from 4 to 10 beats) that follow each premature contraction of the ventricles that is caused by an induced premature atrial contraction. A determination of whether T-wave alternans are present is made based on the measured T-wave metrics.

In still other embodiments, a patient's vagus nerve is stimulated to simulate premature contractions of the ventricles, and at least one metric (e.g., T-wave amplitude) of T-waves is measured in a specified number of beats (e.g., anywhere from 4 to 10 beats) that follow each simulated premature contraction of the ventricles. A determination of whether T-wave alternans are present is made based on the measured T-wave metrics.

Examples of other T-wave metrics that can be measured (i.e., besides T-wave amplitude) include T-wave width, T-wave slope, T-wave area, T-wave morphology, QT interval, and evoked QT interval.

This description is not intended to be a complete description of, or limit the scope of, the invention. Other features, aspects, and objects of the invention can be obtained from a review of the specification, the figures, and the claims.

DETAILED DESCRIPTION OF THE INVENTION

The following detailed description of the present invention refers to the accompanying drawings that illustrate exemplary embodiments consistent with this invention. Other embodiments are possible, and modifications may be made to the embodiments within the spirit and scope of the present invention. Therefore, the following detailed description is not meant to limit the invention. Rather, the scope of the invention is defined by the appended claims.

It would be apparent to one of skill in the art that the present invention, as described below, may be implemented in many different embodiments of hardware, software, firmware, and/or the entities illustrated in the figures. Any actual software and/or hardware described herein is not limiting of the present invention. Thus, the operation and behavior of the present invention will be described with the understanding that modifications and variations of the embodiments are possible, given the level of detail presented herein.

Exemplary ICD

Figure 1:
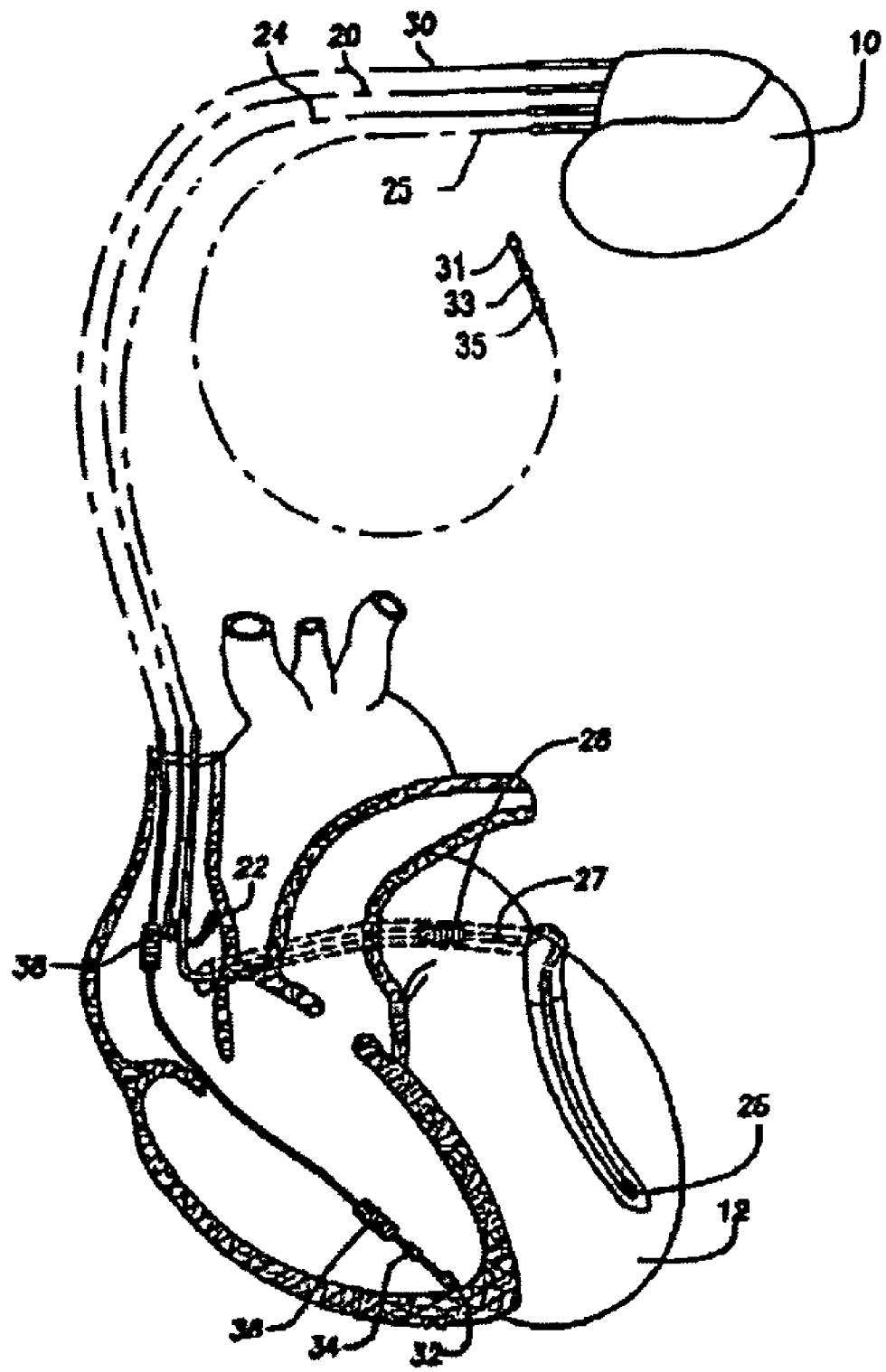
FIG. 1 is a simplified diagram illustrating an exemplary ICD in electrical communication with a patient's heart by means of three leads suitable for delivering multi-chamber stimulation and pacing therapy, and a fourth lead suitable for delivering vagal stimulation.
Figure 2:
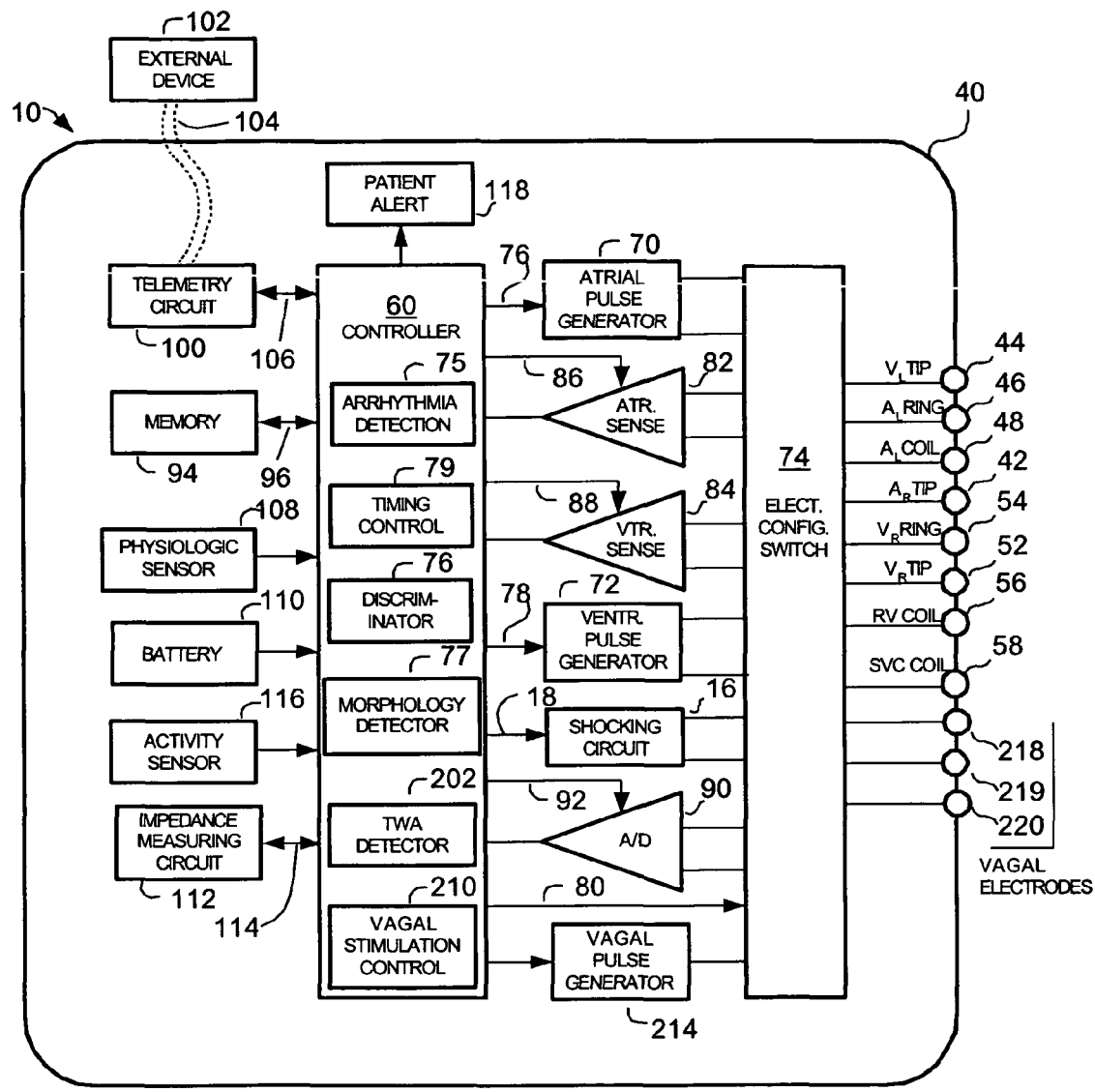
FIG. 2 is a functional block diagram of an exemplary ICD that can provide cardioversion, defibrillation, and pacing stimulation in four chambers of a heart, and detect the presence of T-wave alternans, in accordance with an embodiment of the present invention.

Before describing the invention in detail, it is helpful to describe an example environment in which the invention may be implemented. The present invention is particularly useful in the environment of an implantable cardiac device that can monitor electrical activity of a heart and deliver appropriate electrical therapy, for example, pacing pulses, cardioverting and defibrillator pulses, and drug therapy, as required. Implantable cardiac devices include, for example, pacemakers, cardioverters, defibrillators, implantable cardioverter defibrillators, and the like. The term "implantable cardiac device" or simply "ICD" is used herein to refer to any implantable cardiac device. FIGS. 1 and 2 illustrate such an environment in which embodiments of the present invention can be used.

Referring first to FIG. 1, an exemplary ICD 10 is shown in electrical communication with a patient's heart 12 by way of three leads, 20, 24 and 30, suitable for delivering multi-chamber stimulation and pacing therapy. To sense atrial cardiac signals and to provide right atrial chamber stimulation therapy, ICD 10 is coupled to implantable right atrial lead 20 having at least an atrial tip electrode 22, which typically is implanted in the patient's right atrial appendage.

To sense left atrial and ventricular cardiac signals and to provide left- chamber pacing therapy, ICD 10 is coupled to "coronary sinus" lead 24 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

ICD 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, right ventricular lead 30 is transvenously inserted into heart 12 so as to place the right ventricular tip electrode 32 in the right ventricular apex so that RV coil electrode 36 will be positioned in the right ventricle and SVC coil electrode 38 will be positioned in the SVC. Accordingly, right ventricular lead 30 is capable of receiving cardiac signals and delivering stimulation in the form of pacing and shock therapy to the right ventricle.

In FIG. 1, ICD 10 is also shown as being in electrical communication with the patient's heart 12 by way of a vagal stimulation lead 25, having, e.g., three vagal stimulation electrodes 31, 33, and 35 capable of delivering stimulation bursts to the patient's vagus nerve. Alternatively, vagal stimulation electrodes 31, 33, and 35 can be positioned in the epicardial fat pad near the sinoatrial (SA) node. Based on the description herein, one skilled in the relevant art(s) will understand that the invention can be implemented by positioning vagal stimulation electrodes 31, 33, and 35 in alternate locations, such as in proximity to the cervical vagus, or implanted near or inside the SVC, the inferior vena cava (IVC), or the coronary sinus (CS), where they are also capable of delivering stimulation bursts to the patient's vagus nerve.

FIG. 2 shows a simplified block diagram of ICD 10, which is capable of treating both fast and slow arrhythmias with stimulation therapy, including cardioversion, defibrillation, and pacing stimulation. While a particular multi-chamber device is shown, it is shown for illustration purposes only, and one of skill in the art could readily duplicate, eliminate or disable the appropriate circuitry in any desired combination to provide a device capable of treating the appropriate chamber(s) with the desired cardioversion, defibrillation and pacing stimulation.

A housing 40 of ICD 10, shown schematically in FIG. 2, is often referred to as the "can," "case" or "case electrode" and may be programmably selected to act as the return electrode for all "unipolar" modes. Housing 40 may further be used as a return electrode alone or in combination with one or more of coil electrodes, 28, 36, and 38 for shocking purposes. Housing 40 further includes a connector (not shown) having a plurality of terminals, 42, 44, 46, 48, 52, 54, 56, 58, 218, 219 and 220 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to atrial tip electrode 22.

To achieve left chamber sensing, pacing and shocking, the connector includes at least a left ventricular tip terminal (VL TIP) 44, a left atrial ring terminal (AL RING) 46, and a left atrial shocking terminal (AL COIL) 48, which are adapted for connection to left ventricular ring electrode 26, left atrial tip electrode 27, and left atrial coil electrode 28, respectively.

To support right chamber sensing, pacing, and shocking the connector also includes a right ventricular tip terminal (VR TIP) 52, a right ventricular ring terminal (VR RING) 54, a right ventricular shocking terminal (RV COIL) 56, and an SVC shocking terminal (SVC COIL) 58, which are configured for connection to right ventricular tip electrode 32, right ventricular ring electrode 34, RV coil electrode 36, and SVC coil electrode 38, respectively.

The connector is also shown as including vagal lead terminals (VAGAL ELECTRODES) 218, 219, and 220, which are configured for connection to vagal stimulation electrodes 31, 33, and 35, respectively, to support the delivery of vagal stimulation bursts.

At the core of ICD 10 is a programmable microcontroller 60, which controls the various modes of stimulation therapy. As is well known in the art, microcontroller 60 typically includes one or more microprocessor, or equivalent control circuitry, designed specifically for controlling the delivery of stimulation therapy and can further include RAM or ROM memory, logic and timing circuitry, state machine circuitry, and I/O circuitry. Typically, microcontroller 60 includes the ability to process or monitor input signals (data) as controlled by a program code stored in a designated block of memory. The details of the design of microcontroller 60 are not critical to the present invention. Rather, any suitable microcontroller 60 can be used to carry out the functions described herein. The use of microprocessor-based control circuits for performing timing and data analysis functions are well known in the art.

Representative types of control circuitry that may be used with the invention include the microprocessor-based control system of U.S. Pat. No. 4,940,052 (Mann et. al.) and the state-machines of U.S. Pat. Nos. 4,712,555 (Sholder) and 4,944,298 (Sholder). For a more detailed description of the various timing intervals used within the ICD's and their interrelationship, see U.S. Pat. 4,788,980 (Mann et. al.). The '052, '555, '298 and '980 patents are incorporated herein by reference.

As shown in FIG. 2, an atrial pulse generator 70 and a ventricular pulse generator 72 generate pacing stimulation pulses for delivery by right atrial lead 20, right ventricular lead 30, and/or coronary sinus lead 24 via an electrode configuration switch 74. It is understood that in order to provide stimulation therapy in each of the four chambers of the heart, atrial and ventricular pulse generators 70 and 72 may include dedicated, independent pulse generators, multiplexed pulse generators, or shared pulse generators. Pulse generators 70 and 72 are controlled by microcontroller 60 via appropriate control signals 71 and 78, respectively, to trigger or inhibit the stimulation pulses.

Also shown in FIG. 2, is a vagal pulse generator 214 that is controlled by vagal stimulation control 210 (within microcontroller 60) via a control signal 212, to trigger or inhibit the delivery of vagal stimulation pulses.

Microcontroller 60 further includes timing control circuitry 79, which is used to control pacing parameters (e.g., the timing of stimulation pulses) as well as to keep track of the timing of refractory periods, PVARP intervals, noise detection windows, evoked response windows, alert intervals, marker channel timing, etc., which are well known in the art. Examples of pacing parameters include, but are not limited to, atrio-ventricular (AV) delay, interventricular (RV-LV) delay, atrial interconduction (A-A) delay, ventricular interconduction (V-V) delay, and pacing rate.

Switch 74 includes a plurality of switches for connecting the desired electrodes to the appropriate I/O circuits, thereby providing complete electrode programmability. Accordingly, switch 74, in response to a control signal 80 from microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to right atrial lead 20, coronary sinus lead 24, and right ventricular lead 30, through switch 74 for detecting the presence of cardiac activity in each of the four chambers of the heart. Accordingly, the atrial (ATR. SENSE) and ventricular (VTR. SENSE) sensing circuits 82 and 84 may include dedicated sense amplifiers, multiplexed amplifiers, or shared amplifiers. Switch 74 determines the "sensing polarity" of the cardiac signal by selectively closing the appropriate switches, as is also known in the art. In this way, a clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables ICD 10 to deal effectively with the difficult problem of sensing the low amplitude signal characteristics of atrial or ventricular fibrillation. Such sensing circuits, 82 and 84, can be used to determine cardiac performance values used in the present invention.

The outputs of atrial and ventricular sensing circuits 82 and 84 are connected to microcontroller 60 which, in turn, are able to trigger or inhibit atrial and ventricular pulse generators, 70 and 72, respectively, in a demand fashion in response to the absence or presence of cardiac activity, in the appropriate chambers of the heart. Sensing circuits 82 and 84, in turn, receive control signals over signal lines 86 and 88 from microcontroller 60 for purposes of measuring cardiac performance at appropriate times, and for controlling the gain, threshold, polarization charge removal circuitry (not shown), and timing of any blocking circuitry (not shown) coupled to the inputs of sensing circuits 82 and 86.

For arrhythmia detection, ICD 10 utilizes the atrial and ventricular sensing circuits 82 and 84 to sense cardiac signals to determine whether a rhythm is physiologic or pathologic. The timing intervals between sensed events (e.g., P-waves, R-waves, and depolarization signals associated with fibrillation are then classified by microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Microcontroller 60 utilizes arrhythmia detector 75 and morphology detector 77 to recognize and classify arrhythmia so that appropriate therapy can be delivered. The morphology detector 77 may also be used to detect signal morphologies that are useful for detecting T-wave alternans, in accordance with embodiments of the present invention described below. The arrhythmia detector 75 and morphology detector 77 can be implemented within the microcontroller 60, as shown in FIG. 2. Thus, these elements can be implemented by software, firmware, or combinations thereof. It is also possible that all, or portions, of these detectors can be implemented using hardware.

Cardiac signals are also applied to the inputs of an analog-to-digital (A/D) data acquisition system 90. Data acquisition system 90 is configured to acquire intracardiac electrogram signals, convert the raw analog data into a digital signal, and store the digital signals for later processing and/or telemetric transmission to an external device 102. Data acquisition system 90 is coupled to right atrial lead 20, coronary sinus lead 24, and right ventricular lead 30 through switch 74 to sample cardiac signals across any pair of desired electrodes.

Data acquisition system 90 can be coupled to microcontroller 60, or other detection circuitry, for detecting an evoked response from heart 12 in response to an applied stimulus, thereby aiding in the detection of "capture." Capture occurs when an electrical stimulus applied to the heart is of sufficient energy to depolarize the cardiac tissue, thereby causing the heart muscle to contract. Microcontroller 60 detects a depolarization signal during a window following a stimulation pulse, the presence of which indicates that capture has occurred. Microcontroller 60 enables capture detection by triggering ventricular pulse generator 72 to generate a stimulation pulse, starting a capture detection window using timing control circuitry 79 within microcontroller 60, and enabling data acquisition system 90 via a control signal 92 to sample the cardiac signal that falls in the capture detection window and, based on the amplitude, determines if capture has occurred. Additionally, microcontroller 60 can detect cardiac events, such as premature contractions of ventricles, and the like.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

Microcontroller 60 is further coupled to a memory 94 by a suitable data/address bus 96, wherein the programmable operating parameters used by microcontroller 60 are stored and modified, as required, in order to customize the operation of ICD 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to heart 12 within each respective tier of therapy.

The operating parameters of ICD 10 may be non-invasively programmed into memory 94 through telemetry circuit 100 in telemetric communication with external device 102, such as a programmer, transtelephonic transceiver, or a diagnostic system analyzer. Telemetry circuit 100 is activated by microcontroller 60 by a control signal 106. Telemetry circuit 100 advantageously allows intracardiac electrograms and status information relating to the operation of ICD 10 (as contained in microcontroller 60 or memory 94) to be sent to external device 102 through established communication link 104.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734, entitled "Efficient Generation of Sensing Signals in an Implantable Medical Device such as a Pacemaker or ICD" (McClure et al.), which patents are hereby incorporated herein by reference.

ICD 10 further includes a physiologic sensor 108 that can be used to detect changes in cardiac performance or changes in the physiological condition of the heart. Accordingly, microcontroller 60 can respond by adjusting the various pacing parameters (such as rate, AV Delay, RV-LV Delay, V-V Delay, etc.). Microcontroller 60 controls adjustments of pacing parameters by, for example, controlling the stimulation pulses generated by the atrial and ventricular pulse generators 70 and 72. While shown as being included within ICD 10, it is to be understood that physiologic sensor 108 may also be external to ICD 10, yet still be implanted within or carried by the patient. More specifically, sensor 108 can be located inside ICD 10, on the surface of ICD 10, in a header of ICD 10, or on a lead (which can be placed inside or outside the bloodstream).

Also shown in FIG. 2 is an activity sensor 116. The activity sensor 116 (e.g., an accelerometer) can be used to determine the activity of the patient. Such information can be used for rate responsive pacing, or, in accordance with embodiments of the present invention, to determine whether the patient is sufficiently at rest such that certain baseline measurements can be obtained. If the sensor 116 is a multi-dimensional accelerometer, then posture information can also be extracted. The following patents, which are incorporated herein by reference, describe exemplary activity sensors that can be used to detect activity of a patient (some also detect posture): U.S. Pat. No. 6,658,292 to Kroll et al., entitled "Detection of Patient's Position and Activity Status using 3D Accelerometer-Based Position Sensor"; U.S. Pat. No. 6,466,821 to Kroll et al., entitled "Orientation of Patient's Position Sensor using External Field"; and U.S. Pat. No. 6,625,493 to Pianca et al., entitled "AC/DC Multi-Axis Accelerometer for Determining Patient Activity and Body Position." Simple activity sensors employ a piezoelectric crystal or a cantilever beam having a film of a piezoelectric polymer adhered to a surface of the beam. These are just a few exemplary types of activity sensors 116, which are not meant to be limiting.

The ICD 10 may also include a magnet detection circuitry (not shown), coupled to microcontroller 60. It is the purpose of the magnet detection circuitry to detect when a magnet is placed over ICD 10. A clinician may use the magnet to perform various test functions of ICD 10 and/or to signal microcontroller 60 that the external programmer 102 is in place to receive or transmit data to microcontroller 60 through telemetry circuit 100.

As further shown in FIG. 2, ICD 10 can have an impedance measuring circuit 112, which is enabled by microcontroller 60 via a control signal 114. The known uses for an impedance measuring circuit 112 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to switch 74 so that any desired electrode may be used. The impedance measuring circuit 112 is not critical to the present invention and is shown only for completeness.

In the case where ICD 10 is intended to operate as a cardioverter, pacer or defibrillator, it must detect the occurrence of an arrhythmia and automatically apply an appropriate electrical therapy to the heart aimed at terminating the detected arrhythmia. To this end, microcontroller 60 further controls a shocking circuit 16 by way of a control signal 18. The shocking circuit 16 generates shocking pulses of low (up to about 0.5 Joules), moderate (about 0.5-10 Joules), or high energy (about 11 to 40 Joules), as controlled by microcontroller 60. Such shocking pulses are applied to the patient's heart 12 through at least two shocking electrodes (e.g., selected from left atrial coil electrode 28, RV coil electrode 36, and SVC coil electrode 38). As noted above, housing 40 may act as an active electrode in combination with RV electrode 36, or as part of a split electrical vector using SVC coil electrode 38 or left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of about 5-40 Joules), delivered asynchronously (since R-waves may be too disorganized to be recognize), and pertaining exclusively to the treatment of fibrillation. Accordingly, microcontroller 60 is capable of controlling the synchronous or asynchronous delivery of the shocking pulses.

ICD 10 additionally includes a battery 110, which provides operating power to a load that includes all of the circuits shown in FIG. 2.

TWA Detection

Referring back to FIG. 2, in accordance with embodiments of the present invention, microcontroller 60 includes a T-wave alternan (TWA) detector 202, which as described in more detail below, can detect the presence of T-wave alternans. The TWA detector 202 can be implemented within the microcontroller 60, as shown in FIG. 2. Thus, TWA detector 202 can be implemented by software, firmware, or combinations thereof. It is also possible that all, or portions, of TWA detector 202 can be implemented using hardware. Further, it is possible that all, or portions, of TWA detector 202 be implemented external to the microcontroller 60. In an embodiment, TWA detector 202 triggers data acquisition circuit 90 and timing control circuit 79 to record IEGM signal information following intrinsic, induced or simulated premature contractions of the ventricles. TWA detector 202 can measure T-wave metrics, such as T-wave amplitude, T-wave amplitude, T-wave width, T-wave slope, T-wave area, T-wave morphology, QT interval, evoked QT interval, etc. in the IEGM signal generated by the sensing circuits of the data acquisition system 90. TWA detector 202 can also trigger implantable device 10 to respond appropriately when T-wave alternans are detected, as will be explained in more detail below. Additionally, in conjunction with a telemetry circuit 100, TWA detector 202 can be configured to deliver status information, relating to the patient's T-wave alternans, to an external device 102 through an established communication link 104. TWA detector 202 may also trigger a patient or physician alert in response to detecting T-wave alternans. For example, a patient alert 118, which produces a vibratory or auditory alert, may be triggered by the TWA detector 202.

T-wave alternans have been demonstrated in many studies to be strong predictor of mortality, independent of left ventricular ejection fraction (LVEF). It has been generally believed that an elevated constant heart rate is a requirement for the detection of T-wave alternans. However, a recent work published by Bullinga et al., entitled "Resonant Pacing Improves T-wave Alternans Testing in Patients with Dilated Cardiomyopathy" (Heart Rhythm v1:S129, 2004) revealed a more robust detection with "resonant pacing" scheme. In this technique, TWA with higher amplitudes were detected by pacing at a relatively shorter interval periodically once every fourth cycle during a moderately fast and constant pacing routine. However, Bullinga's scheme still requires that a patient be paced at an elevated heart rate, which for various reasons is not always desirable. Additionally, in Bullinga's technique the heart is perturbed continuously for a certain period in order to get a response, and then the response is scaled and translated into myocardial stability.

The inventor or the present invention believes that T-wave amplitudes will also be elevated following intrinsic premature contractions of the ventricles when the myocardium is electrically unstable, and thus, that T-wave alternans can be detected by monitoring T-waves in a predetermined number of beats (e.g., 2 to 10 beats) that follow intrinsic premature contractions of the ventricles. While these embodiments of the present invention can be used even when there is not a moderately fast and/or constant pacing routine, they can also be used when intrinsic premature ventricular contractions occur during a pacing routing (at normal or moderately fast rates). Additionally, the techniques of the present invention can also be used when a patient's intrinsic heart rate is not elevated, as well as when a patient's intrinsic heart rate is elevated.

Figure 3A:
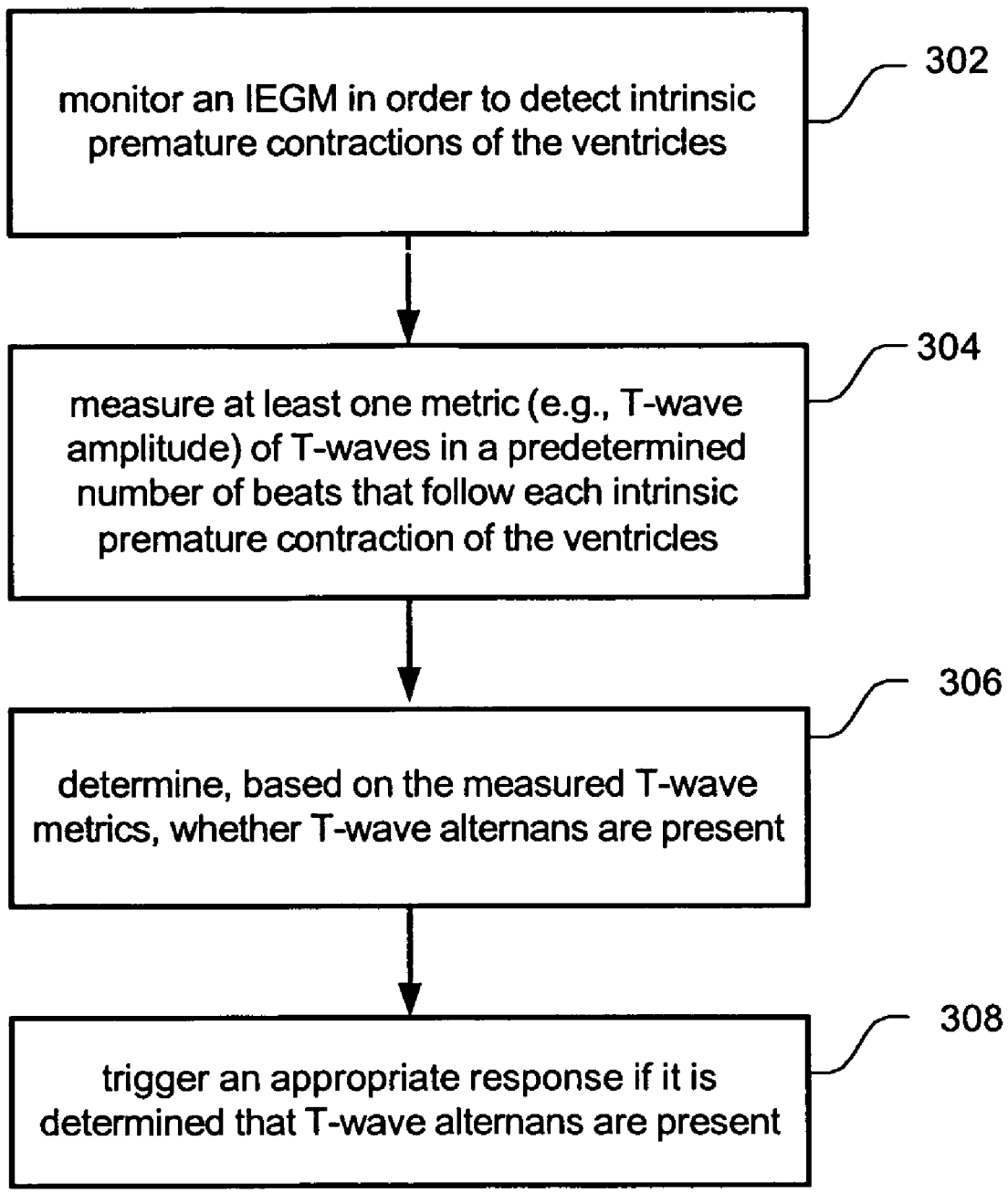
FIG. 3A is a high-level flow diagram that is useful for describing embodiments of the present invention in which T-wave metrics are measured following intrinsic premature contractions of the ventricles, for the purpose of determining whether T-wave alternans are present.

Embodiments of the present invention that relate to monitoring for T-wave alternans following intrinsic premature contractions of the ventricles, will now be summarized with reference to the high level flow diagram of A. In FIG. 3A, a flow diagram is shown describing an overview of the operation and novel features implemented in one embodiment of the device 10. In this flow diagram, and the other flow diagrams described herein, the various algorithmic steps are summarized in individual "blocks". Such blocks describe specific actions or decisions that are made or carried out as the algorithm proceeds. Where a microcontroller (or equivalent) is employed, the flow diagrams presented herein provide the basis for a "control program" that may be used by such a microcontroller (or equivalent) to effectuate the desired control of the stimulation device. Those skilled in the art may readily write such a control program based on the flow diagrams and other descriptions presented herein.

Referring to FIG. 3A, at a step 302 an IEGM is monitored for the purpose of detecting intrinsic premature contractions of the ventricles. Since it is well known how to detect intrinsic premature contractions of the ventricles, there is no need to describe step 302 in additional detail. At a step 304, at least one metric is measured of T-waves in a predetermined number of beats (e.g., 2 to 10 beats) that follow each of the detected intrinsic premature contractions of the ventricles. The metric measured at step 304 can be, e.g., T-wave amplitude, T-wave slope, T-wave area, T-wave width, T-wave timing, T-wave morphology, QT interval, evoked QT interval, Twave positive/negative slopes and durations, etc. Based on the measured T-wave metrics, there is a determination at step 306 of whether T-wave alternans are present. T-wave alternans (TWA), as defined herein, are any magnitude of alternation in one or more metric of T-waves, of two or more consecutive heart beats, beyond a specified minimum threshold. Such a threshold is preferably set such that it can distinguish between alternations that are due to actual changes in a metric of T-waves, as opposed to changes due to noise and/or changes due to misalignments. Such misalignments can occur if a T-wave detector does not mark the same location as the T-wave every time (meaning every beat). It is noted that this definition of T-wave alternans is broader than other definitions that have been proposed in the art.

Exemplary algorithms for determining whether T-wave alternans are present are discussed below. However, it is noted that alternative TWA algorithms can be used, while still being within the spirit and scope of the present invention. In a specific implementation, the algorithm looks for intrinsic premature contractions of the ventricles at step 302. At step 304, after each detected intrinsic premature contraction of the ventricles, a T-wave metric is measured for T-waves of the next M beats (and likely stored in memory 94), where M is an integer between about 2 and 10, inclusive. As mentioned above, such T-wave metrics can include one or more of T-wave amplitude, T-wave slope, T-wave area, T-wave width, T-wave timing, T-wave morphology, QT interval, evoked QT interval, T-wave positive/negative slopes and durations, etc. At step 306, after a total of N intrinsic premature contractions of the ventricles have occurred and the T-wave metrics associated with each have been measured (and likely stored), a T-wave alternan detection algorithm can be enabled. The number N is an integer that can be as low as 1, as large as 1000 (or even larger) but is preferably at least as large as 50.

Assume for example that M=4 and N=50. This would mean that after the detection of an intrinsic premature contraction of the ventricles, T-wave metrics of the next 4 beats are measured and stored in memory, until 50 intrinsic premature contractions of the ventricles are detected. This would result in T-wave metrics being obtained for a total of 200 T-waves. At that point, a T-wave detection algorithm uses the stored T-wave metrics to determine whether T-wave alternans are present.

In accordance with an embodiment of the present invention, if an intrinsic premature contraction of the ventricles is not immediately preceded by at least a specified number of (e.g., 3) consecutive non-premature contractions of the ventricles, then the measured metrics for the T-waves that follow that premature contraction of the ventricles should not be used for the determining whether T-wave alternans are present. This is because a few consecutive intrinsic premature contractions of the ventricles behave like a short run of a ventricular tachycardia (VT), which affects T-waves in a different manner than an isolated premature contraction of the ventricles. This feature can be accomplished in a variety of ways. In one embodiment, metrics of T-waves that follow an intrinsic premature contraction of the ventricles are not measured and/or saved, where that premature contraction of the ventricles is not immediately preceded by at least the specified number of (e.g., 3) consecutive non-premature contractions of the ventricles. In another embodiment, such metrics are measured and stored, but they are not used in the determination of whether T-wave alternans are present. In a further embodiment, such T-wave metrics are measured, but never stored, and thus are not used in determining whether T-wave alternans are present.

Embodiments of the present invention are not directed to the specific techniques that are used to detect the presence of T-wave alternans at step 306 (or at steps 406 and 606 discussed below) after T-wave metrics have been measured. Rather, certain embodiments of the present invention, as can be appreciated from the discussion above, can be thought of as relating to identifying which T-waves should be used in a T-wave detection algorithm. Certain embodiments, as explained below, also relate to causing T-waves (that should be used in a T-wave detection algorithm) on-demand and/or at regular intervals, while preferably not increasing the likelihood of an arrhythmia. Nevertheless, for completion, exemplary techniques are described below that can be used to detect the presence of T-wave alternans at step 306 (or at steps 406 and 606 discussed below) based on the T-wave metrics measured at step 304 (or at steps 404 and 604 discussed below). However, it is noted that embodiments of the present invention should not be limited to the specific techniques described.

In one example, using the T-wave metrics measured at step 304, step 306 can include determining an average T-wave metric (e.g., an average of T-wave amplitude) for the odd numbered T-waves (e.g., the 1st and 3rd T-waves following an intrinsic premature contraction of the ventricles) and an average T-wave metric for the even numbered T-waves (e.g., the 2nd and 4th T-waves following an intrinsic premature contraction of the ventricles). A difference between the odd and even averages can then determined, and the difference can be compared to a threshold to determine if T-wave alternans are present. If the difference (which is an example of a magnitude of alternation) is less than the threshold, then it can be determined that T-wave alternans are not present. If the difference (i.e., the magnitude of alternation) is greater than the threshold, then it can be determined the T-wave alternans are present. It is also possible to have multiple thresholds such that in addition to determining whether T-wave alternans are present, changes in magnitudes of alternations can be determined. This can be used, e.g., to determine a degree of the T-wave alternans. This can also be used for tracking the progression of a disease that influences the electrical stability of the myocardium. Additionally, a degree of the T-wave alternans (or more generally, magnitudes of alternation) can be used as an index of the level of risk for an impending ventricular arrhythmia.

In another example, the difference between the T-wave metrics (e.g., T-wave amplitudes) of successive beats can be determined, and a histogram of the T-wave amplitude differences can be created. For example, assume T-wave amplitudes are measured for 4 beats that follow each detected intrinsic premature contraction of the ventricles. For each 4 beat set, the difference between T-wave amplitudes of the 1st and 2nd beats, the 2nd and 3rd beats, and the 3rd and 4th beats can be determined. Then, it can be determined if the shape of the histogram forms a "double peak mountain" or an upside down "W" centered at about zero. This can be accomplished, e.g., by searching for local maxima's within the histogram. When two local maxima's are found at opposite polarities, e.g., at around +/−0.1 mV, there is a determination that T-wave alternans are present.

For this next example, assume that after the detection of an intrinsic premature contraction of the ventricles, T-wave metrics of the next 4 beats are measured and stored in memory, until 50 intrinsic premature contractions of the ventricles are detected. This would result in T-wave metrics being obtained for a total of 200 T-waves. One option would be to ensemble average the 50 sets of 4 beats and come up with an averaged representation of a 4-beat set. The presence of T-wave alternans can then be determined from this 4-beat set.

Another option would be to determine, for each 4 beat set, the difference between T-wave amplitudes of the 1st and 2nd beats, the 2nd and 3rd beats, and the 3rd and 4th beats, resulting in three differences for each 4 beat set (i.e., a first difference between the metrics for 1st and 2nd beast, a second difference between the metrics for the 2nd and 3rd beats, and a third difference between the metrics for the 3rd and 4th beats). Assuming such differences (which are examples of magnitudes of alternation) are determined for each of 50 separate 4 beat sets, then the first difference of each of the 50 sets can be averaged to produce an average first difference, the second difference of each of the 50 sets can be averaged to produce an average second difference, and the third difference of each of the 50 sets can be average to produce an average third difference. The presence of T-wave alternans can then be determined from the average first difference, the average second difference and the average third difference.

Assuming again that after the detection of an intrinsic premature contraction of the ventricles, T-wave metrics of the next 4 beats are measured and stored in memory, until 50 intrinsic premature contractions of the ventricles are detected, resulting in T-wave metrics being obtained for a total of 200 T-waves. Also assume that the measured T-wave metric is T-wave amplitude. A plurality of T-wave amplitudes that follow intrinsic non-premature contractions of the ventricles are also measured and averaged to produce a baseline. Using this baseline, it is then determined if each individual T-wave measurement (of the beat sets following premature contractions of the ventricles) is substantially equal to the baseline, less than the baseline, or greater than the baseline. There is then a determination of whether a pattern indicative of the presence of T-wave alternans exists. For example, if the number of T-wave measurements greater than the baseline is substantially equal to the number of T-wave amplitudes less than the baseline, and each number is greater than a given minimum number (e.g., 50), than there is a determination that T-wave alternans are present. Additional details of this algorithm are provided in commonly assigned U.S. patent application Ser. No. 10/186,069, which was incorporated herein by reference above.

These are just a few examples of the ways in which the presence of T-wave alternans can be detected at step 306, based on the T-wave metrics measured at step 304. One of ordinary skill in the art will appreciate that many other different techniques can be used, while still being within the spirit and scope of the present invention.

Still referring to FIG. 3A, as shown at step 308, one or more response can be triggered if T-wave alternans are determined to be present. In accordance with an embodiment of the present invention, information related to the T-wave alternans can be stored. This can include, for example, storing amplitude, slope, timing, and/or duration information relating to the T-wave alternans. Such information can be continually, or from time to time, automatically uploaded to an external device (e.g., 102). Such an external device can be located, e.g., in the patients' home, and the information can be transmitted (e.g., through telephone lines or the Internet) to a medical facility where a physician can analyze the information. Alternatively, the external device can be located at a medical facility, and the information can be uploaded when the patient visits the facility.

As mentioned above, T-wave alternans are a known predictor of arrhythmic events such as tachyarrhythmias. Accordingly, in an embodiment, a patient is alerted (e.g., using alert 118) when T-wave alternans are detected. Such an alert could be a vibratory or auditory alert that originates from within the implantable device 10. Alternatively, the implantable device 10 may wirelessly transmit an alert to an external device that produces a visual or auditory alert that a patient can see or hear. The alert may inform that patient that he should rest, or if the patient is operating some type of dangerous machinery (e.g., a car), that the patient should stop what they are doing. By alerting the patient to rest, it is possible the a tachyarrhythmia may be avoided, or if it does occur, the patient will be less dangerous to themselves and others if the patient is resting when the tachyarrhythmias occurs (as opposed, e.g., to driving a car).

Additionally or alternatively, the patient can be instructed to take medication when alerted. In still another embodiment, a physician or other person (e.g., a caregiver, guardian or relative of the patient) is alerted whenever the presence of T-wave alternans is detected.

In further embodiments, therapy can be triggered in response to detecting the presence of T-wave alternans. One type of therapy would be for an implanted device (e.g., device 10) to stimulate the patient's vagus nerve, in an attempt to prevent an arrhythmia from occurring. In another embodiment, the implanted device, if appropriately equipped, can deliver appropriate drug therapy. In still another embodiment, the implanted device, if appropriately equipped, can deliver appropriate pacing therapy. In still another embodiment, the implantable device, if cable of delivering shock therapy, can begin to charge its capacitors in case the patient goes into ventricular fibrillation and needs shock therapy. These are just a few examples of the types of responses that can be performed upon detection of T-wave alternans. One of ordinary skill in the art would understand from the above description that other response are also possible, while still being within the spirit and scope of the present invention.

An advantage of the embodiments of the present invention described with reference to FIG. 3A is that these embodiments can be performed by an implantable device (such as an implantable monitoring device) that does not include stimulation capabilities. This, however, does not mean that these embodiments can not be implemented by an implantable device that does provide for stimulation capabilities, as can be appreciated from the above discussion. Another advantage of these embodiments is that they enable T-wave alternans to be monitored for without requiring elevation of a patient's heart rate through exercise or overdrive pacing. In other words, with embodiments of the present invention the state of a heart can be assessed in its sort of native and un-paced state. This is especially advantageous with patients that are for whatever reason physically incapacitated or limited such that elevating their heart rate would be difficult and/or dangerous. Nevertheless, as stated above, these embodiments can also be used if a patient's heart happens to be elevated.

Figure 3B:
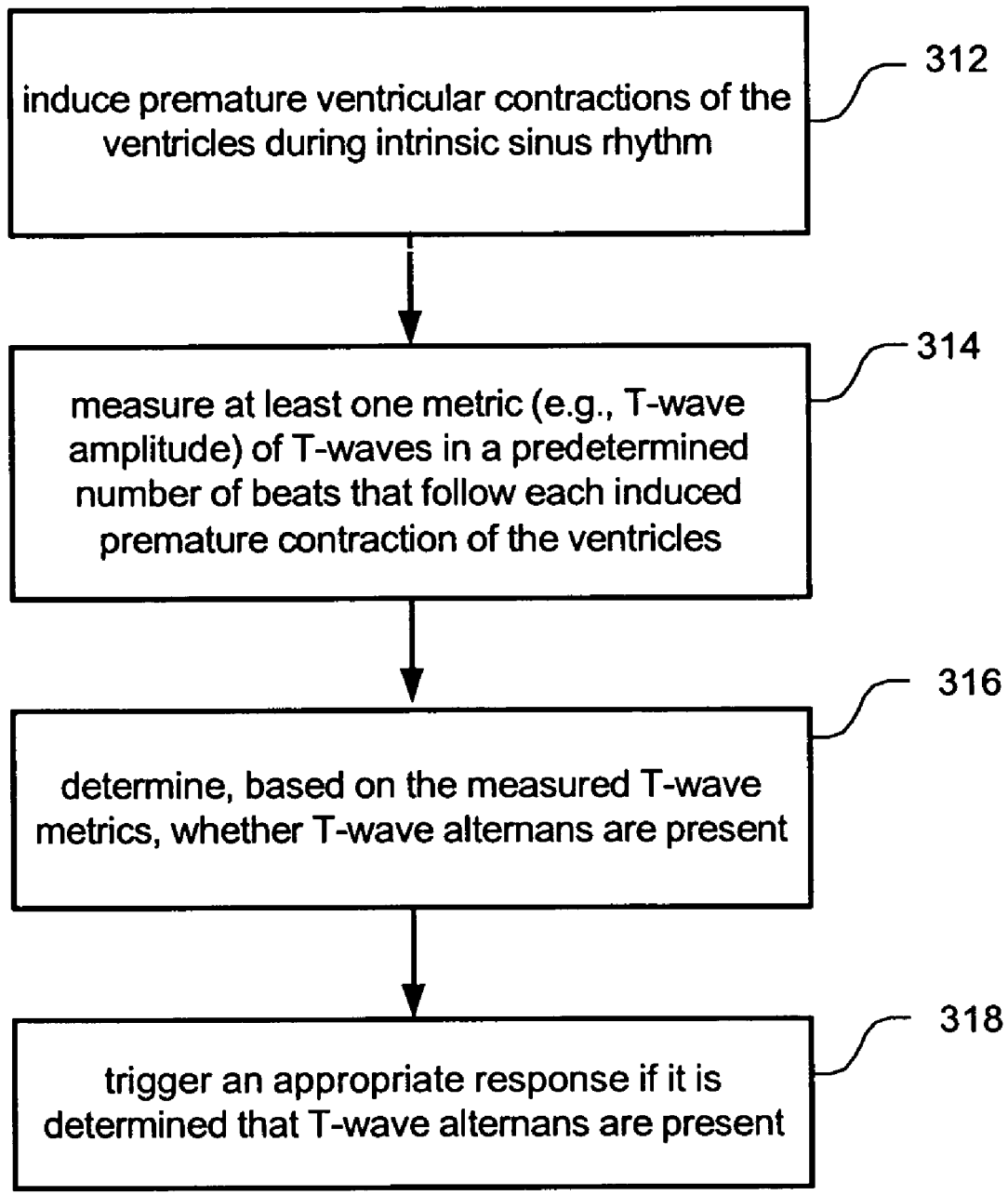
FIG. 3B is a high-level flow diagram that is useful for describing embodiments of the present invention in which premature contractions of the ventricles are induced during intrinsic sinus rhythm, for the purpose of determining whether T-wave alternans are present.

However, a disadvantage of detecting T-wave alternans based on monitored T-waves that follow intrinsic premature contractions of the ventricles, as described above with reference to FIG. 3A, is that this technique cannot be executed on-demand or at regular intervals. One way to overcome this disadvantage is to artificially induce premature contractions of the ventricles during intrinsic sinus rhythm, so that T-waves that follow the induced premature contractions of the ventricles can be monitored for the purpose of detecting T-wave alternans. Such embodiments are summarized in the high level flow diagram of FIG. 3B. Referring back to FIG. 2, a premature contraction of the ventricles can be induced during intrinsic sinus rhythm, e.g., by applying a single premature stimulus to the one of the ventricles using the ventricular pulse generator 72. An advantage of these embodiments is that they can be executed on-demand and at regular intervals, without requiring elevation of a patient's heart rate through exercise or overdrive pacing. These embodiments, like the previous embodiments, are advantageous with patients that are for whatever reason physically incapacitated or limited such that elevating their heart rate would be difficult and/or dangerous. A potential disadvantage of artificially inducing premature contractions of the ventricles in this manner, however, is that it may inadvertently cause an arrhythmia.

The inventor of the present invention believes that T-wave amplitudes will also be elevated following premature contractions of the ventricles that are caused by inducing premature atrial contractions (PACs). However, premature contractions of the ventricles that are caused in this manner should not increase the chance of an arrhythmia. Accordingly, in accordance with specific embodiments of the present invention, premature contractions of the ventricles are caused, on demand, by inducing premature atrial contractions (PACs), and T-wave metrics are measured of T-waves in a specified number of beats that follow such premature contractions of the ventricles. In such an approach, the patient's right or left atrium is stimulated prematurely to artificially induce a PAC. Referring back to FIG. 2, this can be accomplished by applying a single premature stimulus to the atrium using the pulse generator 70. The induced PAC conducts through the AV node and into the ventricles, thereby causing the ventricles to prematurely contract, which results in a corresponding drop in blood pressure. An advantage of this technique is that it can be executed on-demand and at regular intervals, and is not likely to cause an arrhythmia. These embodiments of the present invention are summarized in the high level flow diagram of FIG. 4.

Figure 4:
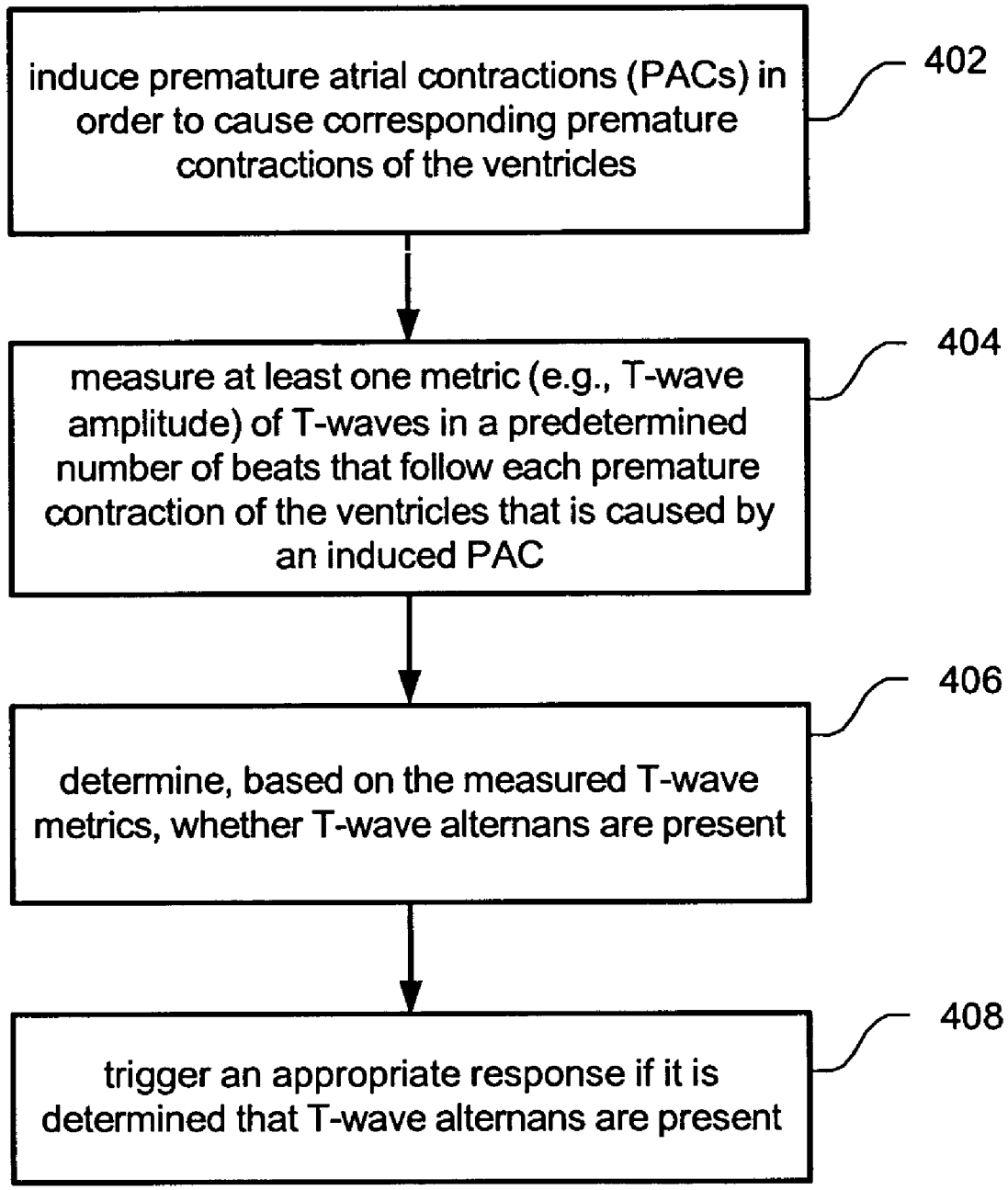
FIG. 4 is a high-level flow diagram that is useful for describing embodiments of the present invention in which T-wave metrics are measured following premature contractions of the ventricles caused by induced premature atrial contractions, for the purpose of determining whether T-wave alternans are present.

Referring to FIG. 4, at a step 402, premature atrial contractions (PACs) are induced to thereby cause corresponding premature contractions of the ventricles. As just mentioned, each PAC can be induced, e.g., by applying a single premature stimulus to the atrium. At least 3 non-premature contractions of the ventricles, and preferably at least 10 non-premature contractions of the ventricles, occur between each induced PAC. At a step 404, at least one T-wave metric is measured for T-waves of a predetermined number of beats (e.g., 2 to 10 beats) that follow each premature contraction of the ventricles caused by an induced PAC. Based on the measured T-wave metrics, there is a determination at step 406 of whether T-wave alternans are present. At step 408, a response can be triggered when the presence of T-wave alternans is detected. Since steps 406 and 408 are similar to steps 306 and 308 described above, these steps need not be described again in detail.

In still other embodiments of the present invention, rather than waiting for intrinsic premature contractions of the ventricles, or inducing premature contractions of the ventricles (i.e., by artificially stimulating a ventricle, or artificially inducing a PAC that conducts through the AV node and into the ventricles), premature contractions of the ventricles are "simulated", as will now be described with reference to FIG. 5.

Figure 5:
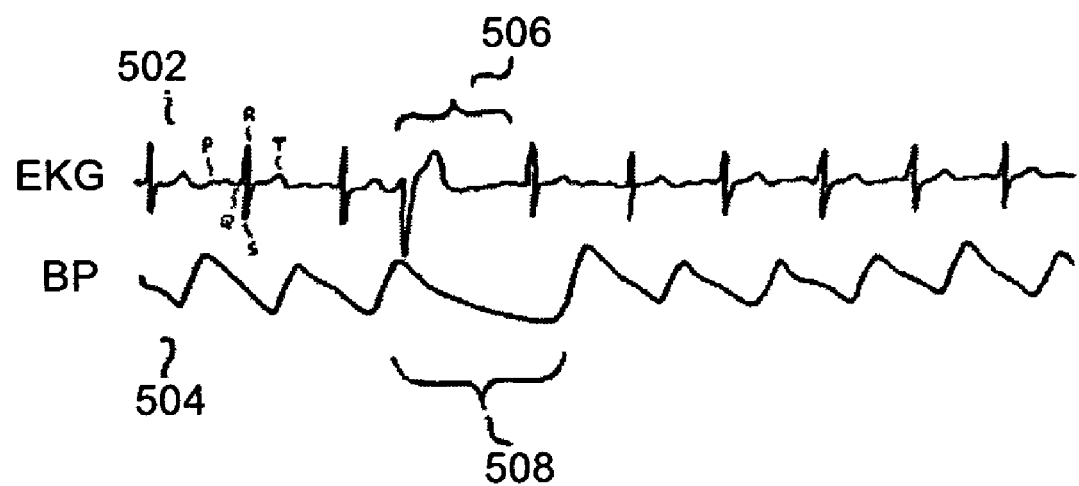
FIG. 5, which illustrates a portion of an IEGM and a blood pressure waveform, is useful for explaining how premature contractions of the ventricles can be simulated, by stimulating a patients vagus nerve, in accordance with embodiments of the present invention.

Referring to FIG. 5, an exemplary IEGM trace 502 and blood pressure trace 504 are shown. As can be appreciated from FIG. 5, each cycle of the IEGM waveform 502, which corresponds to a heart beat, includes a P wave that is a normally small positive wave caused by the beginning of a heart beat. Following the P wave there is a portion which is substantially constant in amplitude. The QRS complex of the IEGM then normally occurs after the substantially constant portion, beginning with a Q wave that is normally a small negative deflection, which is then immediately succeeded by the R wave that is a rapid positive deflection. Following the R wave, the QRS complex is completed with an S wave that is generally characterized by a small positive inflection in the ECG signal. Following the S wave is a T-wave, which is separated from the S wave by the ST segment. A premature contraction of the ventricles is shown within the exemplary IEGM trace 502. Also shown is the resulting disturbance 508 in the arterial blood pressure trace 504. Such an arterial blood pressure disturbance 508 can also be triggered by stimulating a patient's vagus nerve, as was disclosed in commonly invented and assigned U.S. patent application Ser. No. 10/861,747, entitled "System and Method for Using Vagal Stimulation to Assess Autonomic Tone and Risk of Sudden Cardiac Death in an Implantable Cardiac Device," filed Jun. 4, 2004, which is incorporated herein by reference. As explained in the '747 application, a short burst of stimulation to the vagus nerve induces a drop in atrial pressure, which simulates a patient's cardiovascular response to a premature contraction of the ventricles. Accordingly, such stimulation of the vagus nerve will be referred to hereafter as "simulating" a premature contraction of the ventricles. The inventor of the present invention believes that T-wave amplitudes will also be elevated following such "simulated" premature contractions of the ventricles. These embodiments of the present invention are summarized in the high level flow diagram of FIG. 6.

Figure 6:
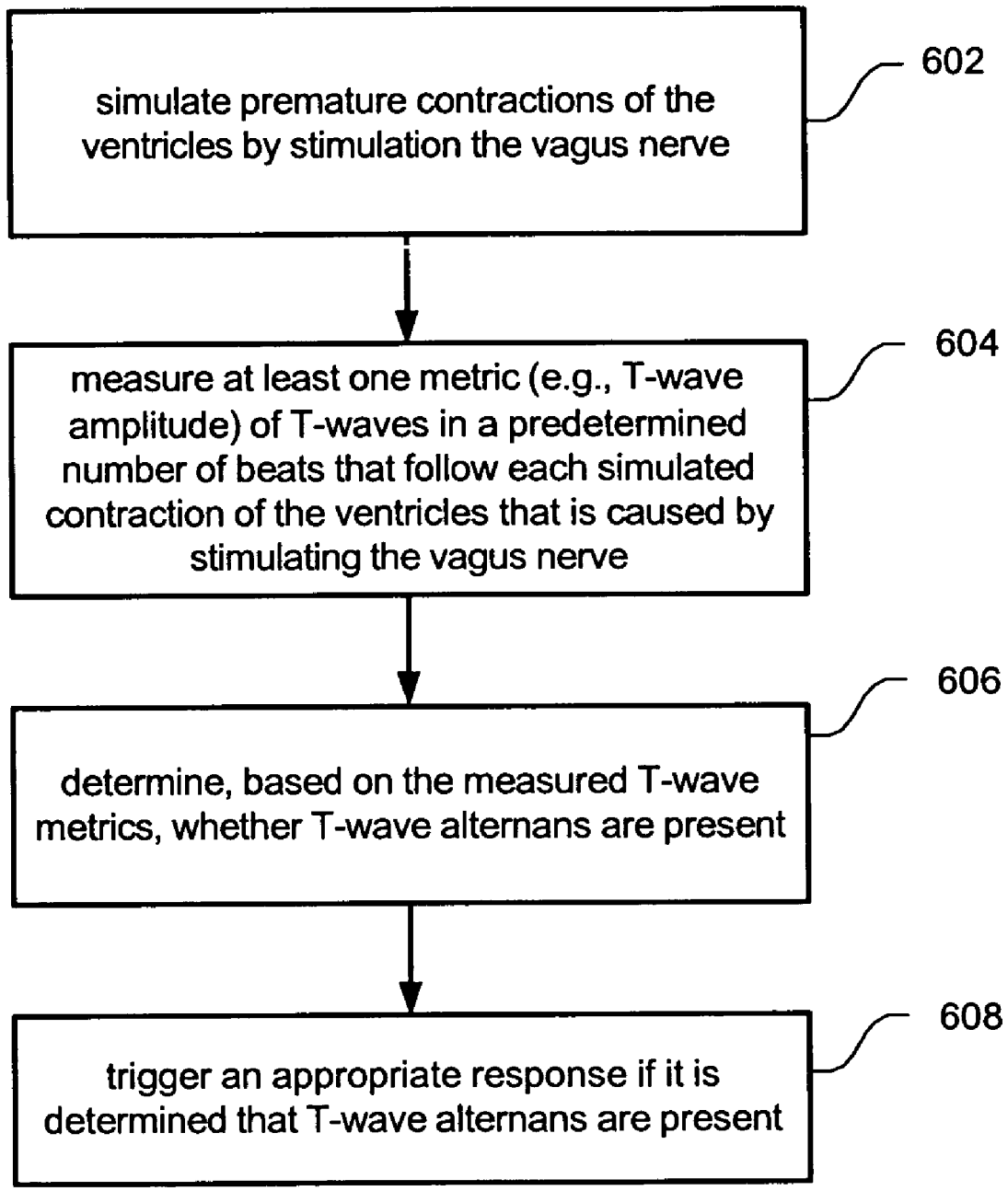
FIG. 6 is a high-level flow diagram that is useful for describing embodiments of the present invention in which T-wave metrics are measured following simulated premature contractions of the ventricles, for the purpose of determining whether T-wave alternans are present, where the simulated premature contractions of the ventricles are caused by stimulating a patients vagus nerve.

Referring to FIG. 6, at a step 602, premature contractions of the ventricles are "simulated" by stimulating a patient's vagal nerve. For example, this is accomplished by delivering, on demand, a short burst of stimulation to the vagus nerve to thereby induces a drop in atrial pressure, which simulates a patient's cardiovascular response to a premature contraction of the ventricles. More specifically, the patient's vagus nerve is stimulated for a duration that simulates compensatory pause 512, shown in FIG. 5, in order to trigger an intrinsic baroreflex response to a drop in blood pressure. Referring back to FIG. 1, the vagal stimulation lead 25 can be used to deliver such stimulation. Referring back to FIG. 2, the vagal pulse generator 214 can produce the stimulation pulses to be delivered by the lead 25. There should be at least 3 beats (and preferably at least 10 beats) in which a premature contraction of the ventricles does not occur between each "simulated" premature contraction of the ventricles. At a step 604, T-waves of a predetermined number of beats (e.g., 2 to 10 beats) that follow each simulated premature contraction of the ventricles (caused by stimulating the vagus nerve) are monitored. Based on the monitored T-waves, there is a determination at step 606 of whether T-wave alternans are present. At step 608, a response can be triggered when the presence of T-wave alternans is detected. Since steps 606 and 608 are similar to steps 306 and 308 described above, these steps need not be described again in detail. An advantage of the embodiments summarized with reference to FIG. 6 is that they can be executed on-demand and at regular intervals, and are not likely to cause an arrhythmia.

In accordance with specific embodiments of the present invention, magnitudes of alternation can be determined based on the metrics of T-waves measured in a specified number of beats that follow detected intrinsic premature contractions of the ventricles (or that follow premature contractions of the ventricles induced during intrinsic sinus rhythm; or that follow premature contractions of the ventricles caused by inducing premature atrial contractions; or that follow simulated premature contractions of the ventricles caused by stimulating the patients vagus nerve; or combinations thereof). For example, magnitudes of alternation can be measures of differences in T-wave metrics (e.g., T-wave amplitude, T-wave width, T-wave slope, T-wave area, T-wave morphology, QT interval and/or evoked QT interval) for alternating beats in the beats of interest. Such magnitudes of alternation are compared to one or more corresponding threshold, which, in accordance with an embodiment, is set to be indicative of electrical instability of the myocardium, and thus, an imminent onset of an arrhythmia. Based on the results of these comparison(s), one or more response can be triggered. If there are multiple metrics (and thus multiple magnitudes of alternation), then there can be multiple corresponding thresholds, with a specific response or responses based on which thresholds are exceeded.

One response can be to store information related to the metrics of T-waves for later retrieval and/or transmission to a physician or other clinician. Another response involves triggering a patient or physician alert that warns of an impending arrhythmia, thereby allowing the patient to respond appropriately. Such an alert could be, e.g., a vibratory or auditory alert that originates from within an implantable device. Alternatively, an implantable device may wirelessly transmit an alert to an external device that produces a visual or auditory alert that a patient can see or hear. The alert may inform that patient that he should rest, or if the patient is operating some type of dangerous machinery (e.g., a car), that the patient should stop what they are doing. Additionally or alternatively, the patient can be instructed to take medication when alerted. In further embodiments, a preventive therapy can be triggered in response to assessing a risk of an impending arrhythmia. One type of therapy would be for an implanted device (e.g., device 10) to stimulate the vagal nerve, in an attempt to slow down the heart rate. Another response would be to deliver an appropriate anti-arrhythmia pacing therapy. In another embodiment, the implanted device, if appropriately equipped, can deliver an appropriate drug therapy. One of ordinary skill in the art would appreciate from the above description that other types of therapies can be triggered. These are just a few examples of the types of responses that can be performed upon assessing a risk of an impending arrhythmia. One of ordinary skill in the art would understand from the above description that other responses are also possible, while still being within the spirit and scope of the present invention.

In further embodiments, changes in magnitudes of alternation are tracked thereby track changes in myocardial electrical stability. This can include recognizing increases in magnitudes of alternations as being indicative of increased electrical instability of the myocardium, and recognizing decreases in magnitudes of alternations as being indicative of increased electrical stability of the myocardium.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

Example embodiments of the methods, systems, and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein.

Thus, the breadth and scope of the present invention should not be limited by any of the above-described exemplary embodiments, but should be defined only in accordance with the following claims and their equivalents.

What is claimed is:

1. In an implantable system, a method for detecting T-wave alternans, comprising:
   (a) detecting at least one intrinsic premature contraction of the ventricles;
   (b) measuring at least one metric of T-waves in a specified number of beats that follow each detected intrinsic premature contraction of the ventricles; and
   (c) determining if the detected intrinsic premature contraction of the ventricles is immediately preceded by at least a specified number of non-premature contractions of the ventricles and further determining, based on the measured T-wave metrics, whether T-wave alternans are present wherein, if the detected intrinsic premature contraction is not immediately preceded by at least the specified number of non-premature contractions then the T-wave metrics following the detected intrinsic premature contraction are either not measured or not used in determining if T-wave alternans are present.

2. The method of claim 1, wherein step (a) includes detecting a plurality of intrinsic premature contractions of the ventricles.

3. The method of claim 2, wherein whenever one of the intrinsic premature contractions of the ventricles detected at step (a) is not immediately preceded by at least a specified number of non-premature contractions of the ventricles, then the T-wave metrics measured at step (b) for the beats that follow that detected intrinsic premature contraction of the ventricles are not used in step (c) when determining whether T-wave alternans are present.

4. The method of claim 1, wherein step (b) comprises measuring a metric of T-waves in M beats that follow each detected intrinsic premature contraction of the ventricles, where M is an integer between 2 and 10, inclusive.

5. The method of claim 1, wherein step (b) includes measuring at least one of the following T-wave metrics:
   T-wave amplitude;
   T-wave width;
   T-wave slope;
   T-wave morphology;
   QT interval; and
   evoked QT interval.

6. An implantable system for detecting T-wave alternans (TWA), comprising:
   means for measuring at least one metric of T-waves in a specified number of beats that follow each detected intrinsic premature contraction of the ventricles;
   a TWA detector means to determine, based on the measured T-wave metrics, and based on the number of non-premature contractions of the ventricles that immediately precede the detected intrinsic premature contraction, whether T-wave alternans are present wherein, if the detected intrinsic premature contraction is not immediately preceded by at least the specified number of non-premature contractions then the T-wave metrics following the detected intrinsic premature contraction are either not measured or not used in determining if T-wave alternans are present.

7. The system of claim 6, further comprising:
   means for detecting intrinsic premature contractions of the ventricles.

8. The system of claim 6, wherein whenever a detected intrinsic premature contraction of the ventricles is not immediately preceded by at least a specified number of non-premature contractions of the ventricles, then the TWA detector does not use the T-wave metrics measured for the beats that follow that detected intrinsic premature contraction of the ventricle when determining whether T-wave alternans are present.

9. The system of claim 6, wherein at least one metric of T-waves is measured in M beats that follow each detected intrinsic premature contraction of the ventricles, where M is an integer between 2 and 10, inclusive.

10. The system of claim 6, where said means for measuring measures at least one of the following T-wave metrics:
    T-wave amplitude;
    T-wave width;
    T-wave slope;
    T-wave morphology;
    QT interval; and
    evoked QT interval.

11. In an implantable system, a method comprising:
    (a) detecting intrinsic premature contractions of the ventricles;
    (b) measuring one or more metrics of T-waves in a specified number of beats that follow each premature contraction of the ventricles detected at step (a);
    (c) determining for each detected intrinsic premature contraction of the ventricles if it is immediately preceded by at least a specified number of non-premature contractions of the ventricles and further determining, based on the measured T-wave metrics, magnitudes of alternation, wherein, for each intrinsic premature contraction detected in step (a) if the detected intrinsic premature contraction is not immediately preceded by at least the specified number of non-premature contractions then the T-wave metrics following the detected intrinsic premature contraction are either not measured or not used in determining magnitudes of alteration;
    (d) comparing the magnitudes of alternation to one or more thresholds; and
    (e) triggering one or more responses based on results of the comparisons performed at step (d).

12. The method of claim 11, wherein one said threshold is set to be a predictor of an imminent arrhythmia.

13. The method of claim 11, wherein step (e) includes triggering an alert.

14. The method of claim 11, wherein step (e) includes triggering anti-arrhythmia therapy.

15. The method of claim 11, wherein step (b) includes measuring at least one of the following T-wave metrics: T-wave amplitude; T-wave slope; T-wave area; T-wave morphology; QT interval; and evoked QT interval.

* * * * *